United States Patent
Alfieri et al.

(10) Patent No.: US 8,529,621 B2
(45) Date of Patent: Sep. 10, 2013

(54) METHODS OF REPAIRING AN ABNORMAL MITRAL VALVE

(75) Inventors: Ottavio Alfieri, Brescia (IT); Francesco Maisano, Milan (IT); Alberto Redaelli, Milan (IT)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/416,929

(22) Filed: Mar. 9, 2012

(65) Prior Publication Data
US 2012/0172983 A1    Jul. 5, 2012

Related U.S. Application Data

(63) Continuation of application No. 12/697,936, filed on Feb. 1, 2010, now abandoned, which is a continuation of application No. 10/742,454, filed on Dec. 18, 2003, now Pat. No. 7,674,286, which is a continuation of application No. 10/144,932, filed on May 15, 2002, now Pat. No. 6,726,717.

(51) Int. Cl.
*A61F 2/24* (2006.01)

(52) U.S. Cl.
USPC .......................... 623/2.36; 623/2.38

(58) Field of Classification Search
USPC .............. 623/1.26, 2.1, 2.36, 2.37, 2.38, 2.11
See application file for complete search history.

(56) References Cited

U.S. PATENT DOCUMENTS

| | | | |
|---|---|---|---|
| 3,656,185 A * | 4/1972 | Carpentier | .................... 623/2.36 |
| 4,055,861 A | 11/1977 | Carpentier et al. | |
| 4,164,046 A | 8/1979 | Cooley | |
| 4,217,665 A | 8/1980 | Bex et al. | |
| 4,275,469 A | 6/1981 | Gabbay | |
| 4,602,911 A | 7/1986 | Ahmadi et al. | |
| 4,790,844 A | 12/1988 | Ovil | |
| 4,914,097 A | 4/1990 | Oda et al. | |
| 4,993,428 A | 2/1991 | Arms | |
| 5,010,892 A | 4/1991 | Colvin et al. | |
| 5,041,130 A | 8/1991 | Cosgrove et al. | |

(Continued)

FOREIGN PATENT DOCUMENTS

| | | |
|---|---|---|
| EP | 0338994 | 10/1989 |
| EP | 0595791 | 5/1994 |

(Continued)

OTHER PUBLICATIONS

Edwards Lifesciences, Carpentier-Edwards Classic Mitral Annuloplasty Ring, Feb. 12, 2001.

(Continued)

*Primary Examiner* — Thomas J Sweet
*Assistant Examiner* — Christopher D Prone
(74) *Attorney, Agent, or Firm* — AnneMarie Kaiser; Guy Cumberbatch

(57) ABSTRACT

The present invention refers to an annular prosthesis for mitral valve. In one of its embodiments the annular prosthesis for mitral valve is made up of a posterior half-ring and an anterior half-ring coupled to each other on a first transverse plane which defines a maximum width section of the prosthesis, characterized in that the ratio between the distance between said anterior half-ring and said posterior half-ring, as measured along a second plane, perpendicular to said first plane and equidistant to said couplings, and said maximum width of the prosthesis is lower than ¾.

20 Claims, 1 Drawing Sheet

(56) References Cited

U.S. PATENT DOCUMENTS

| | | |
|---|---|---|
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,639 B2 | 6/2004 | Lewallen |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,527,647 B2 | 5/2009 | Spence |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0070999 A1 | 3/2005 | Spence |
| 2005/0075727 A1 | 4/2005 | Wheatley |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0149368 A1 | 7/2006 | Spence |
| 2006/0195183 A1 | 8/2006 | Navia et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |

| | | | |
|---|---|---|---|
| 2007/0173930 | A1 | 7/2007 | Sogard et al. |
| 2007/0213582 | A1 | 9/2007 | Zollinger et al. |
| 2007/0255396 | A1 | 11/2007 | Douk et al. |
| 2009/0177278 | A1 | 7/2009 | Spence |
| 2009/0192602 | A1 | 7/2009 | Kuehn |
| 2009/0192603 | A1 | 7/2009 | Ryan |
| 2009/0192604 | A1 | 7/2009 | Gloss |
| 2009/0192605 | A1 | 7/2009 | Gloss et al. |
| 2009/0192606 | A1 | 7/2009 | Gloss et al. |

FOREIGN PATENT DOCUMENTS

| | | |
|---|---|---|
| EP | 0860151 | 8/1998 |
| EP | 1034753 | 9/2000 |
| FR | 2708458 | 2/1995 |
| WO | 9119456 | 12/1991 |
| WO | 9503757 | 2/1995 |
| WO | 9640006 | 12/1996 |
| WO | 9741801 | 11/1997 |
| WO | 9742871 | 11/1997 |
| WO | 9806329 | 2/1998 |
| WO | 9911201 | 3/1999 |
| WO | 9951169 | 10/1999 |
| WO | 9965423 | 12/1999 |
| WO | 0032105 | 6/2000 |
| WO | 0119292 | 3/2001 |
| WO | 0126586 | 4/2001 |
| WO | 0147438 | 7/2001 |
| WO | 0187191 | 11/2001 |
| WO | 0203892 | 1/2002 |
| WO | 03020178 | 3/2003 |
| WO | 03041617 | 5/2003 |
| WO | 2004004607 | 1/2004 |
| WO | 2005004753 | 1/2005 |
| WO | 2005034813 | 4/2005 |
| WO | 2005082278 | 9/2005 |
| WO | 2005110290 | 11/2005 |
| WO | 2006041877 | 6/2006 |
| WO | 2006133186 | 12/2006 |
| WO | 2007050506 | 5/2007 |
| WO | 2007100408 | 9/2007 |
| WO | 2007131513 | 11/2007 |
| WO | 2008058940 | 5/2008 |
| WO | 2008063537 | 5/2008 |
| WO | 2008094469 | 8/2008 |
| WO | 2008098226 | 8/2008 |

OTHER PUBLICATIONS

Seguin, et al., Advance in Mitral Valve Repair Using a Device Flexible in Three Dimensions, ASAIO Journal vol. 42, No. 6, pp. 368-370, 1996.

Adams, David, et al., "Large Annuloplasty Rings Facilitate Mitral Valve Repair in Barlow's Disease," Society of Thoracic Surgeons 42nd Annual Meeting, Jan. 30-Feb. 1, 2006.

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier, et al. "The 'Physio-Ring': An Advanced Concept in Mitral Valve Annuloplasty," Society of Thoracic Surgeons 31st Annual Meeting, Jan. 30-Feb. 2, 1995.

Carpentier-Edwards Classic Annuloplasty Ring With Duraflo Treatment Models 4425 and 4525 for Mitral and Tricuspid Valvuloplasty, Baxter Healthcare Corporation, 1998.

Carpentier-Edwards Physio Annuloplasty Ring, Edwards Lifesciences Corporation, 2003.

Cochran, et al., Effect of Papillary Muscle Position on Mitral Valve Function: Relationship to Homografts, The Society of Thoracic Surgeons, pp. 5155-5161, 1998.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al., Effect of Annular Shape of Leaflet Curvature in Reducing Mitral Leaflet, American Heart Association, Circulation 200; pp. 106-711.

Smolens, et al., Mitral Valve Repair in Heart Failure, The European Journal of Heart Failure 2, pp. 365-371, 2000.

Techniques for 3D Quantative Echocardiography, University of Washington Cardiovascular Research & Training Center Cardiac Imaging Research Lab, pp. 1-5, Oct. 2003.

Watanbe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

Salgo, Effect of annular shape on leaflet curvature in reducing mitral leaflet stress, American Heart Association, Circulation, 2002; 106: 711-717.

* cited by examiner

METHODS OF REPAIRING AN ABNORMAL MITRAL VALVE

RELATED PATENT APPLICATIONS

The present application is a continuation of co-pending Ser. No. 12/697,936, filed Feb. 1, 2010, which is a continuation of Ser. No. 10/742,454, filed Dec. 18, 2003, now U.S. Pat. No. 7,674,286, which is a continuation of Ser. No. 10/144,932 filed May 15, 2002, now U.S. Pat. No. 6,726,717, which claims foreign priority to Italian Patent Application Serial No. MI2001a 001012, filed on May 17, 2001.

FIELD OF THE INVENTION

The present invention refers to an annular prosthesis for mitral valve.

BACKGROUND OF THE INVENTION

The mitral plastic surgery operation includes a series of procedures suitable to re-establish the correct functionality of the mitral valve, when this is affected by congenital or acquired pathology. Among these procedures, the remodelling of the valve annulus is one of the most frequently used manoeuvres in order to complete and/or to strengthen the valve. Remodelling provides for two moments: the reduction of the annular area and the properly said remodelling, that is suitable to re-establish the normal geometric ratios that are found in natural valves free of pathology. The first one of these manoeuvres is usually carried out with the aid of a prosthesis that is appropriately sutured to the natural annulus. The prosthesis for annuloplastic surgery available on the market are of two types. Flexible annular prostheses, made of various materials, that allow a "linear" reduction of the annular circumference, and rigid and semi-rigid annular prostheses made of various materials, that allow the "linear" reduction of the annular circumference and a geometric remodelling so as to re-establish the physiological systolic shape of the annulus. In the case of semi-rigid prostheses they additionally allow a minimum deformation in order to allow the prosthesis to follow the deformations of the annulus-during the cardiac stages.

All the rigid and semi-rigid annular prostheses have a kidney-like or coupled D shape, with an anterior half-ring, rectilinear in first approximation, that gets sutured in correspondence of the joining of the anterior valve leaflet and a curved posterior half-ring that is sutured in correspondence of the joining of the posterior valve leaflet. The shape of the annular prostheses at issue reproduces the configuration of the valve annulus during the ventricular systole, and therefore in the stage of the valve closing. The ratio between minor axis and major axis is approximately ¾ in all the models currently on the market since it reproduces normal anatomical ratios.

Recently the concept of undersizing of mitral valve annuloplasty has been introduced. This procedure is proposed in case of mitral insufficiency due to a reduced movement of the leaflets as in the case of ischaemic mitral valve or dilated cardiomyopathy. The undersizing consists in using a ring smaller than necessary, though still maintaining the ratio of approximately ¾, and it is carried out in order to bring the base of the anterior leaflet even closer to the posterior leaflet in order to increase the coaptation surface (closure).

The Applicants noticed that in certain pathological conditions, there is a need to modify such ratio in order to make the operation of reconstruction of the mitral valve more effective: for instance in order to bring the valve leaflets closer to each other in the case of anatomical or functional tissue deficiency of one or both leaflets. In addition, it has also been observed that anatomical variation that do not correspond to the ratios reported above are frequent in nature.

In view of the state of the art herein described, a scope of the present invention is to provide an annular prosthesis for mitral valve that can meet the different requirements that have been noticed.

SUMMARY OF THE INVENTION

According to present the invention, these and other scopes have been attained by means of an annular prosthesis for mitral valve made up of a posterior half-ring and an anterior half-ring that are coupled to each other on a first transverse plane which defines a maximum width section of the prosthesis, characterised in that the ratio between the distance between said anterior half-ring and said posterior half-ring, as measured along a second plane, perpendicular to said first plane and equidistant to said couplings, and said maximum width of the prosthesis is lower than ¾.

BRIEF DESCRIPTION OF THE DRAWINGS

The characteristics and the advantages of the present invention will become evident from the following detailed description of an embodiment thereof, that is illustrated as a non-limiting example in the enclosed drawings, in which.

DESCRIPTION OF THE PREFERRED EMBODIMENTS

Figure 1:
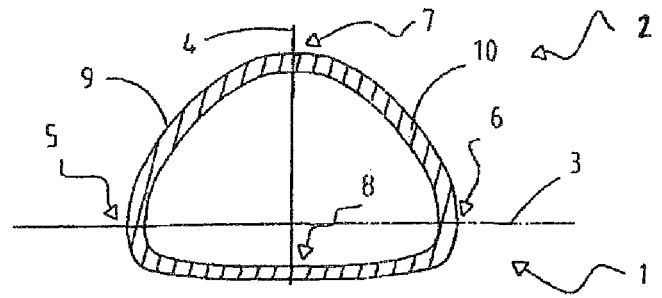
FIG. 1 shows an annular prosthesis for mitral valve according to the known art.

In FIG. 1 a prosthesis for annular mitral valve according to the known art is shown. It has a kidney-like or D-shape, and it is made up of an anterior half-ring 1 rectilinear in first approximation, that is sutured in correspondence of the joining of the anterior valve leaflet 2 and a curved posterior half-ring that is sutured in correspondence of the joining of the posterior valve leaflet. The posterior half-ring 2 and anterior half-ring 1 are coupled at two points 5 and 6 located on a transverse plane 3 that define a maximum width section of the prosthesis. In addition a longitudinal plane 4 is also defined, that intersects the prosthesis at the points 7 and 8, that is arranged perpendicular to the transverse plane 3 and equidistant from the coupling points 5 and 6. The posterior half-ring 2 is thus subdivided in a first lateral zone (left) 9 located between the points 5 and 7, and a second lateral zone (right) 10 located between the points 6 and 7. The intersection points 5, 6 and 7, 8 of the prosthesis respectively with the planes 3 and 4 define the terms for the calculation of the dimensions of the prosthesis. According to the known art, the ratio between the distance between the points 7 and 8, herein also defined as height of the prosthesis, and the distance between the points 5 and 6, herein also defined as width of the prosthesis, is typically equal to ¾.

Figure 2:
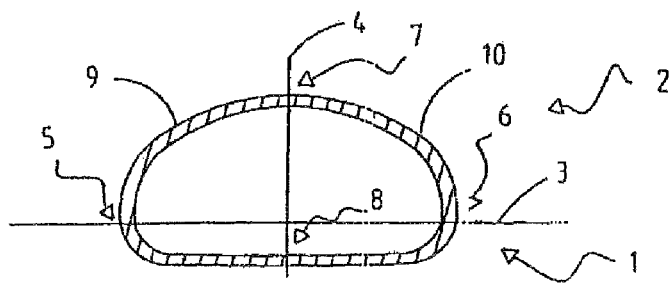
FIG. 2 shows a first embodiment of an annular prosthesis for mitral valve according to the present invention.

In FIG. 2 a first embodiment of an annular prosthesis for mitral valve according to the present invention is shown. It substantially has the same shape as the one rendered in FIG.

1 but the ratio between the height and the width of the prosthesis is lower than ¾, for instance equal to 2.5/4 or equal to ⅔.

For every size of prosthesis two or more reduced ratios can therefore be provided. By size the dimension of the transverse width of the prosthesis is meant; it represents the clinical parameter on the bases of which the prosthesis is selected in each single clinical case in examination, and it is also the identifying parameter for the prosthesis.

The lower ratio as compared with the prostheses currently used for annuloplastic surgery allows its use in selected cases of pathologies that are not treatable in adequate way with conventional prostheses.

The lower ratios in this case have the function to treat pathologies characterised by reduced movement of the leaflets with tethering (stretching towards the cardiac apex) symmetrical (as regards each leaflet) with medium or serious proportions. The reduction of the ratio confers the prosthesis a more "squeezed" shape, that allows a better apposition of the leaflets in selected cases. For instance, in the dilated cardiomyopathy, when the expansion of the left ventricle determines a lateral movement and toward the apex of the papillary muscles, the leaflets stretch toward the cardiac apex and the apposition is thus lacking at central level. A possible sizing, in addition, must respect an anatomical requirement: the anterior half-ring 1 (the base for the implant of the front leaflet) is anatomically fixed and not modifiable, and therefore, the sizing should not be applied to this structure, that is to the width of the prosthesis. The maintaining of a normal fore width of the prosthesis, associated with the reduction of the height allows an undersizing that is less inclined to deformation of the fore leaflet, therefore reducing the risk of residual insufficiency.

Figure 3:
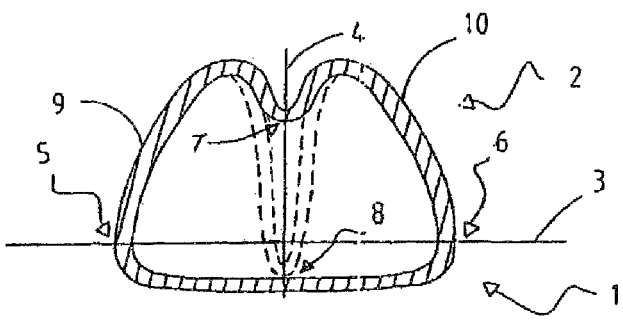
FIG. 3 shows a second embodiment of an annular prosthesis for mitral valve according to the present invention.

In FIG. 3 a second embodiment of an annular prosthesis for mitral valve according to the present invention is shown. In this case the natural ratio height/width of ¾ is maintained in order to define the curving radii of the two lateral parts of the anterior half-ring. In the central zone, in proximity of the point 7, the distance between the posterior half-ring 1 and the front half-ring 2 is reduced, with the aim of obtaining a height/width ratio lower than ¾. The central zone of the posterior half-ring 2 therefore takes a configuration that recalls the dog bone or gull wing shape and increases the coaptation at central level by limiting the annular reduction at level of the commisure.

In some extreme cases, it could be useful to make the distance between the two half-rings in the central zone equal to zero, in order to obtain an eight-shape configuration, in order to improve the coaptation at central level. This remodelling simulates the double orifice operation, in which the leaflets are joined at the centre of the valve in order to force the central coaptation. This prosthesis could also be used with this type of technique in order to reduce the stress on the suture and in order to minimise the reduction of the valve area.

Figure 4:
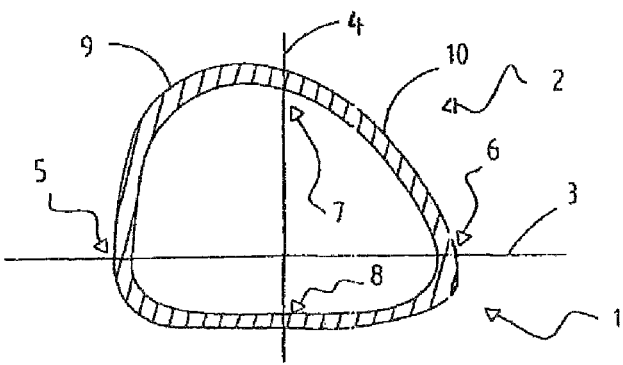
FIG. 4 shows a third embodiment of an annular prosthesis for mitral valve according to the present invention.

In FIG. 4 a third embodiment of an annular prosthesis for mitral valve according to the present invention is shown.

In this embodiment the curving radius of one of the lateral zones, for instance the second lateral zone (right) 10, is increased so as to induce a selective increase of the competence in correspondence of the valve sector with reduced mobility of the leaflets (bad asymmetric apposition of the leaflets as in ischaemic pathology). It is thus obtained that one part of the prosthesis, for instance the first lateral zone (left) 9, maintains a configuration substantially similar to the traditional prosthesis and one part, for instance the second lateral zone (right) 10, gets a sized configuration. In other words the distance between the middle point of the first lateral zone (left) 9 and the longitudinal plane 4 is greater than the distance between the middle point of the second lateral zone (right) 10 and the longitudinal plane The prosthesis, according to the present invention, can be made of an inert material that is highly tolerated by the human organism and can have a resistance that is appropriated to the use and that can substantially maintain the shape given to it.

What is claimed is:

1. A method of correcting the functionality of a patient's mitral valve in a mitral annulus having an anterior leaflet and a posterior leaflet, comprising:
   providing an annular prosthetic ring made of a material that can substantially maintain an implanted shape defining a curved posterior section contiguous with a generally rectilinear anterior section and together forming a periphery oriented around a central flow axis, wherein in plan view as seen along the flow axis the prosthetic ring has a transverse plane that defines a maximum width representing an identifying size parameter of the prosthetic ring corresponding to the dimension of the base of the patient's anterior leaflet in systole, and a longitudinal plane perpendicular to the transverse plane that bisects the anterior and posterior sections, the prosthetic ring having a height from the anterior section to the posterior section along the longitudinal plane; and
   implanting the prosthetic ring at the patient's mitral valve such that the curved posterior section lies along the mitral annulus at the base of the posterior leaflet and the generally rectilinear anterior section lies along the mitral annulus at the base of the anterior leaflet;
   wherein the prosthetic ring has a reduced height to maximum width ratio relative to a normal height to width ratio found in the annulus of natural valves free of pathology so that when implanted the prosthetic ring squeezes the mitral annulus along the longitudinal axis such that the posterior valve leaflet and anterior valve leaflet move toward each other relative to their normal spacing as found in a natural valve free of pathology while the mitral annulus in the transverse direction and the maximum width of the prosthetic ring remain substantially unchanged.

2. The method of claim 1, wherein the prosthetic ring is symmetrical across the longitudinal plane.

3. The method of claim 1, wherein the prosthetic ring is asymmetrical across the longitudinal plane.

4. The method of claim 3, wherein the curved posterior section on one side of the longitudinal plane has a radius of curvature that is smaller than on the other side of the longitudinal plane.

5. The method of claim 1, wherein the curved posterior section and generally rectilinear anterior section of the prosthetic ring together form a generally D-shaped periphery.

6. The method of claim 1, wherein the prosthetic ring has a height to maximum width ratio that is equal to 2.5/4.

7. The method of claim 1, wherein the prosthetic ring has a height to maximum width ratio is equal to ⅔.

8. A method of correcting the functionality of a patient's mitral valve in a mitral annulus having an anterior leaflet and a posterior leaflet, the mitral annulus having a transverse dimension in systole along the base of the patient's anterior leaflet and a longitudinal dimension perpendicular to the transverse dimension and between the bases of the two leaflets, the method comprising:
   selecting an annular prosthetic ring from a choice of prosthetic rings made of a material that can substantially maintain an implanted shape, the prosthetic ring selected having an identifying size corresponding to the transverse dimension of the mitral annulus, wherein each prosthetic ring defines a posterior section contiguous with an anterior section and forming a periphery oriented around a central flow axis, wherein in plan view as seen along the flow axis the prosthetic ring has a maximum width dimension along a major axis perpendicular to a height dimension along a minor axis that bisects the anterior and posterior sections, wherein the maximum width dimension is approximately equal to the transverse dimension; and implanting the prosthetic ring at the patient's mitral valve such that the curved posterior section lies along the mitral annulus at the base of the posterior valve leaflet and the generally rectilinear anterior section lies along the mitral annulus at the base of the anterior valve leaflet;

wherein the prosthetic ring has a reduced height dimension to maximum width dimension ratio relative to a normal height to width ratio found in the annulus of natural valves free of pathology so that when implanted the prosthetic ring reduces the longitudinal dimension such that the posterior valve leaflet and anterior valve leaflet move toward each other relative to their normal spacing as found in a natural valve free of pathology while the transverse dimension of the annulus and the maximum width of the prosthetic ring remain unchanged.

9. The method of claim 8, wherein the prosthetic ring is symmetrical across the minor axis.

10. The method of claim 8, wherein the prosthetic ring is asymmetrical across the minor axis.

11. The method of claim 10, wherein the curved posterior section on one side of the minor axis has a radius of curvature that is smaller than on the other side of the minor axis.

12. The method of claim 8, wherein the prosthetic ring has a height dimension to maximum width dimension ratio that is equal to $2.5/4$.

13. The method of claim 8, wherein the prosthetic ring has a height dimension to maximum width dimension ratio is equal to $2/4$.

14. A method of correcting the functionality of a patient's mitral valve having an annulus, an anterior leaflet and a posterior leaflet, comprising implanting a prosthetic ring made of a material that can substantially maintain an implanted shape at the patient's mitral valve such that when implanted, the prosthetic ring squeezes the mitral annulus along the longitudinal axis relative its normal shape as found in a natural valve free of pathology such that the posterior valve leaflet and anterior valve leaflet move toward each other relative to their normal spacing as found in a natural valve free of pathology while the mitral annulus in the transverse direction and the maximum width of the prosthetic ring remain substantially unchanged.

15. The method of claim 14, wherein the annular prosthetic ring defines a periphery oriented around a central flow axis, wherein in plan view as seen along the flow axis the prosthetic ring has a maximum width dimension along a major axis perpendicular to a minor axis that bisects the anterior and posterior sections, and the method includes implanting the prosthetic ring at the patient's mitral valve such that the maximum width dimension is parallel to the base of the anterior valve leaflet.

16. The method of claim 15, wherein the prosthetic ring is symmetrical across the minor axis.

17. The method of claim 15, wherein the prosthetic ring is asymmetrical across the minor axis.

18. The method of claim 17, wherein the curved posterior section on one side of the minor axis has a radius of curvature that is smaller than on the other side of the minor axis.

19. The method of claim 15, wherein the prosthetic ring has a height dimension along the minor axis and the ratio of the height dimension to maximum width dimension is equal to $2.5/4$.

20. The method of claim 15, wherein the prosthetic ring has a height dimension along the minor axis and the ratio of the height dimension to maximum width dimension is equal to $2/4$.

* * * * *